(12) United States Patent
Nakamura et al.

(10) Patent No.: US 6,858,405 B1
(45) Date of Patent: Feb. 22, 2005

(54) PROCESS FOR PRODUCING PROTEIN HYDROLYZATE

(75) Inventors: Michinobu Nakamura, Kawasaki (JP);
Mitsuyoshi Seki, Kawasaki (JP);
Miyoko Nawata, Kawasaki (JP);
Hidetsugu Nakazawa, Kawasaki (JP);
Hideki Okamura, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/674,280

(22) PCT Filed: Apr. 23, 1999

(86) PCT No.: PCT/JP99/02171

§ 371 (c)(1),
(2), (4) Date: Dec. 21, 2000

(87) PCT Pub. No.: WO99/57302

PCT Pub. Date: Nov. 11, 1999

(30) Foreign Application Priority Data

Apr. 30, 1998 (JP) ............................................ 10/121029
Apr. 30, 1998 (JP) ............................................ 10/121030

(51) Int. Cl.[7] .............................. C12P 21/06; C12P 1/02; C12N 1/14
(52) U.S. Cl. ...................... 435/68.1; 435/171; 435/911; 435/913; 435/918
(58) Field of Search ................................ 435/68.1, 171, 435/911, 913, 918; 424/115

(56) References Cited

U.S. PATENT DOCUMENTS

| | | | | |
|---|---|---|---|---|
| 3,655,396 A | * | 4/1972 | Goto et al. ....................... | 99/9 |
| 4,808,419 A | * | 2/1989 | Hsu ............................. | 426/13 |
| 5,888,561 A | * | 3/1999 | Niederberger et al. ........ | 426/20 |
| 6,045,819 A | * | 4/2000 | Takebe ........................ | 424/442 |

FOREIGN PATENT DOCUMENTS

| | | | |
|---|---|---|---|
| JP | 50019996 | * | 3/1975 |
| JP | 52-079084 | | 7/1977 |
| JP | 6-245790 | | 9/1994 |
| WO | WO 95/28853 | * | 11/1995 |

OTHER PUBLICATIONS

Muramatsu et al. Nippon Jozo Kyokaishi. (1992), 87(3), pp. 219–223.*

* cited by examiner

*Primary Examiner*—Vera Afremova
(74) *Attorney, Agent, or Firm*—Oblon, Spivak, McClelland, Maier & Neustadt, P.C.

(57) ABSTRACT

The present invention relates to a method which can prevent browning of hydrolyzed protein obtained by enzymatic hydrolysis of vegetable protein material.

A vegetable protein material containing saccharides is mixed with the fungal culture and is subjected to enzymatic hydrolysis in a liquid reaction system. The reaction is conducted first at a temperature ranging from 15° C. to 39° C. with aeration and agitation, and then, after stopping the aeration, the reaction is conducted and completed at a temperature ranging from 40° C. to 60° C.

7 Claims, 2 Drawing Sheets

PROCESS FOR PRODUCING PROTEIN HYDROLYZATE

TECHNICAL FIELD

The present invention relates to a method for producing hydrolyzed protein. More specifically, it relates to a method for producing hydrolyzed protein, wherein in a step of enzymatically hydrolyzing a vegetable protein material containing a protein in a solid state, the hydrolysis is conducted in a specific manner, whereby the resulting hydrolyzate is not browned or a period of time that lapses until the resulting hydrolyzate is browned can markedly be prolonged.

BACKGROUND ART

With respect to a process for obtaining amino acids by enzymatically hydrolyzing a protein starting material containing a vegetable protein in a solid state, a large number of processes have been already known.

For example, JP-A-51-35461 describes a process for producing a liquid seasoning comprising, in combination, a first step of reacting modified de-fatted soybeans having a soluble nitrogen index of 50 or less with an alkaline protease having a pH of from 9 to 12 for 2 hours, thereby solubilizing and extracting 70% or more of a protein-derived nitrogen component to conduct solid-liquid separation, and a second step of subjecting the extracted to hydrolysis with a peptidase in a sealed container at from 40° C. to 60° C.

Further, JP-A-6-125734 describes an enzyme preparation which is obtained from an organic solvent-dipped product of koji formed through solid culture of a microorganism and which contains an exopeptidase obtained through autolysis of the koji, and a process for producing a proteinous liquid seasoning, which comprises reacting an animal or vegetable protein material with protein solubilizing enzymes, and then reacting the reaction product with a exopeptidase-containing enzyme preparation.

Still further, JP-A-9-75032 describes a process for producing a seasoning, wherein when koji for soy sauce is charged in the presence of alcohol for enzymatic hydrolysis at from 35° C. to 45° C., evaporation is forcibly conducted such that the alcohol concentration in the completion of the hydrolysis is 2% or less, and this hydrolyzate is fermented and aged.

Furthermore, JP-A-9-121807 describes a multi-purpose seasoning having a high glutaminate content and having a flavor peculiar to an acid-hydrolysis seasoning without a soy sauce smell and a brewing smell. This seasoning is prepared by simultaneously conducting the cultivation of a koji mold (Aspergillus) and the hydrolysis of proteins in the medium by the enzymes contained in the culture of the koji mold in the absence of salt or in the presence of a small amount of salt.

However, the problem has remained that when the hydrolyzate produced by these conventional processes is stored, coloring occurs within a relatively short period of time, and it is browned rapidly, with the result that the commercial value thereof is notably reduced.

Any known processes for producing amino acids by enzymatically hydrolyzing a protein material containing a solid protein have involved problems that microorganisms other than those as the enzyme source in the hydrolysis step, so-called contaminants are grown, reducing the quality of hydrolyzates and decreasing the yield of amino acids. In order to solve the problems, the presence of bacteriostatic materials such as alcohol, sodium chloride and ethyl acetate has been employed in the hydrolysis step in the conventional processes. In these processes, an additional step of separating and removing the bacteriostatic materials after the completion of the hydrolysis step is required. Especially when the presence of sodium chloride is employed as a bacteriostatic means, it has been quite difficult to remove sodium chloride to less than an appropriate concentration without reducing the quality of the resulting hydrolyzate. Further, it has been almost impossible to avoid occurrence of a so-called brewing smell or soy sauce smell in the product obtained through the hydrolysis step in the presence of the bacteriostatic materials, which results in extremely limiting the use range of the hydrolyzed protein obtained.

In addition, in the conventional processes as well, an approach has naturally been attempted in which contaminants incorporated or contained in a protein material containing a solid protein or a microbial culture as the enzyme source are removed or killed, and the hydrolysis step is then conducted. The process in which the starting material is subjected to the proteolysis reaction after the sterilization is said to be relatively easy on a laboratory scale. However, in the industrial mass-production, it involves quite serious problems such as the control of contaminants in the sterilization step and the proteolysis step.

DISCLOSURE OF THE INVENTION

One object in the present invention is to establish a method in which the browning of a hydrolyzed protein obtained by enzymatically hydrolyzing a protein material containing a vegetable protein in a solid state is prevented to stably maintain the commercial value thereof over a long period of time.

Another object of the present invention is to provide a process for producing hydrolyzed protein which is useful as a multi-purpose seasoning material or a multi-purpose food material without contamination with germs even in the absence of a bacteriostatic substance, which process can be practiced in the industrial mass-production.

In order to solve the problem, the present inventors have conducted a large number of experiments and assiduous studies regarding a method for enzymatic hydrolysis of protein materials containing various vegetable proteins and a relationship of the conditions thereof and the browning of the resulting hydrolyzate. Consequently, they have obtained the following new findings (1) to (3).

(1) Occurrence and progression of the hydrolyzate browning is closely related with a concentration of reducing sugars contained in the reaction product immediately after the hydrolysis reaction. That is, when the concentration of reducing sugars is high, the browning occurs immediately after the reaction, and it rapidly proceeds even under an ordinary storage environment.

(2) Once the browning occurs, it is quite difficult to find an effective method for inhibiting the progression of the browning.

(3) The concentration of reducing sugars contained in the reaction product immediately after the hydrolysis can be controlled to less than a predetermined concentration by specifying the hydrolysis method and the conditions thereof. Besides, in the thus-specified hydrolysis method and conditions, the hydrolysis rate of the protein itself and the composition ratio of the resulting amino acids is substantially unchanged.

The present inventors have also obtained the following new findings (4) to (6) with respect to the sterilization of the protein material and the culture medium.

(4) Contaminants grown in the hydrolysis step are those present in the protein material in a solid state and in the microbial culture as the enzyme source.

(5) In case the protein material and the culture medium can completely be sterilized, the hydrolysis step can be conducted substantially in the absence of contaminants.

(6) The sterilization of the protein material and the culture medium is extremely inhibited by the presence of air and bubbles contained therein. In other words, when the heat sterilization is conducted after air and bubbles contained therein are completely removed, the protein material which is substantially in a sterile state and the culture of microorganisms as the enzyme source which is substantially free from contamination with germs can be obtained.

The present inventors have completed the inventions on the basis of these new findings.

That is, the first invention is a method for producing hydrolyzed protein by subjecting a vegetable protein material containing saccharides to enzymatic hydrolysis using a fungal culture in a liquid reaction system, comprising mixing the vegetable protein material with the fungal culture, conducting a reaction first at a temperature ranging from 15° C. to 39° C. with aeration and agitation, and then, after stopping the aeration, conducting and completing the reaction at a temperature ranging from 40° C. to 60° C.

The second invention is the method for producing hydrolyzed protein according to the first invention, wherein the vegetable protein material is selected from the group consisting of wheat gluten, corn gluten, de-fatted soybean and treated products thereof.

The third invention is the method for producing hydrolyzed protein according to the first invention, wherein the reaction which is conducted at a temperature ranging from 15° C. to 39° C. is shifted to the reaction which is conducted at a temperature ranging from 40° C. to 60° C. when from 10% to 60% of the total period of time required from the start-up to the completion of the reaction passes after the start-up of the reaction.

The fourth invention is the method for producing hydrolyzed protein according to the first invention, wherein a ratio of reducing sugars present in the reaction product obtained at the completion of the reaction is adjusted to 5% by weight or less based on the total solid content in the reaction product.

The fifth invention is the method for producing hydrolyzed protein according to the first invention, wherein the preparation of the fungal culture and the enzymatic hydrolysis of the vegetable protein material are conducted in a submerged culture tank-type reaction vessel.

The sixth invention is the method for producing hydrolyzed protein according to the first invention, wherein the vegetable protein material is at least partially in a solid state, and is pulverized to 300 $\mu$m or less prior to the enzymatic hydrolysis, dispersed in hot water at higher than 80° C., subjected to the sterilization immediately after air bubbles contained in the pulverized product are substantially removed.

The present inventions are described in detail below.

The starting material used in the present invention is a vegetable protein material containing saccharides. That is, it is a vegetable protein starring material having a high content of an edible vegetable protein which is at least partially in a solid state, and containing saccharides including starch and various saccharides other than starch, such as glucose, fructose, sucrose and galactose.

The form of these vegetable protein materials used is not particularly limited. Starting materials having the various forms such as powder, granules, pellets, a dispersion in an aqueous solvent and paste, are used. Further, so long as it is the vegetable protein material, its origin is not limited.

Specific examples of the vegetable protein material include starting materials such as wheat gluten, corn gluten, de-fatted soybean, separated soybean protein, separated potato protein and treated products of these vegetable protein materials. Of these vegetable protein materials, wheat gluten and de-fatted soybean are especially important protein materials in the invention.

The treatment of enzymatically hydrolyzing the vegetable protein material is a step of dispersing in an aqueous solvent the sterilized protein material or the protein material kept in a bacteriostatic state, and contacting the dispersion with a fungal culture having a high proteolytic activity in the aqueous solvent to hydrolyze the protein material.

It is important to employ an embodiment of conducting aeration and agitation at the initial stage of the hydrolysis reaction, confirming, after a certain period of time, that the reaction system is in a predetermined state, and then clearly shifting the reaction temperature to a high temperature region and continuing the contact. In this respect, the method is markedly different from an ordinary method for enzymatically hydrolyzing a protein material. Thus, it is a main characteristic feature in the method of the invention.

For practicing this embodiment specifically, it is required that a hydrolysis reaction vessel or tank is provided with at least a temperature control equipment, an aeration equipment and a agitation equipment. In the reaction, a rate of aeration of 1/1 vvm or less is sufficient. The agitation equipment is not particularly limited so long as it corresponds to the size of the reaction vessel and fully withstands a load such as a viscosity of the starting dispersion or the reaction system. Various agitation devices are available. For example, a submerged culture device used in fermentation for amino acid production is an especially preferable reaction device.

The starting material used is pulverized or finely divided so as not to inhibit the agitation procedure, at the time of sterilization of the starting material or just before the hydrolysis reaction. The sterilization treatment is conducted by a method and a device which are ordinarily employed in the fermentation industry. In order to conduct the hydrolysis reaction without germ contamination, cultivation of fungi as the enzyme source is carried out under the non-contamination conditions. Further, as a matter of course, a measure to cope with germ contamination and a management of the process during the reaction step should be perfectly conducted.

It is preferable that the protein material is, before subjected to the proteolysis step, pulverized to a size of 300 $\mu$m or less, and dispersed in hot water at 80° C. or higher. The pulverization of the protein material may be conducted with respect to a dry protein material. However, when it is conducted simultaneously with the treatment of dispersing in hot water the protein material which has been roughly pulverized, the step can continuously be shifted to the sterilization step conveniently.

The conditions of the pulverization and the temperature condition of hot water for dispersion have inductively been determined as a result of many tests on various protein materials. When the pulverization is conducted as much as possible under these conditions and the treatment is conducted at a high temperature of approximately a boiling point, preferable sterilization effects can be expected in the subsequent sterilization step.

That is, when the dispersion containing particles having particle size of 300 µm or more is treated with a heat exchanger, the particles of the protein material in the dispersion are precipitated, and there is a risk that clogging might occur in the flow path of the heat exchanger. Accordingly, the sterilization treatment becomes actually impossible.

Meanwhile, a phenomenon has been found that the viscosity of the dispersion of fine particles of the protein material is abruptly decreased at 80° C. or higher.

FIG. 1 is a line graph showing a relationship of a viscosity and a temperature of a dispersion of wheat gluten in hot water having a concentration of 32% at temperatures ranging from 60° C. to 90° C. In FIG. 1, the ordinate axis indicates a viscosity at regular intervals with a unit of $10^4$ cps (centipoises), and the abscissa axis indicates a temperature at regular intervals with a unit of ° C. In this example, it can be observed that the viscosity is remarkably decreased at a temperature of from 80° C. to 85° C.

One of the technical progresses in the invention exists in this point. That is, the marked improvement of the handleability with the abrupt decrease in the viscosity of the protein material dispersion within the specific temperature range is linked with the effective heat sterilization.

When the protein material is subjected to the pulverization and the hot water dispersion, the dispersion of the protein material shows an emulsified state in many cases. However, the viscosity of the dispersion is not increased, and the dispersion becomes a non-tacky solution having a low viscosity. Consequently, air and bubbles are not included into the dispersion treated.

When the protein material is pulverized and dispersed in hot water, a method and an apparatus that meet the purpose can be employed. For example, a method can be employed in which the powdery protein material is fed to a tank containing an aqueous solution which has been maintained at a predetermined temperature, and fed to an emulsifier while being stirred for emulsification and dispersion.

What is important in the dispersion treatment is to confirm that air and bubbles are not adhered to, nor contained in, the fine particles of the protein material present in the dispersion after the dispersion treatment. At this time, the dispersion after the disppersion treatment is observed in a weak enlarged visual field of a microscope, and it is identified that bubbles are substantially not adhered to the fine particles dispersed and that the fine particles dispersed are brought into direct contact with a liquid phase portion.

In case bubbles are present in the dispersion after the dispersion treatment, no predetermined sterilization effect can be expected even when the high-temperature treatment is conducted in the subsequent sterilization step. Further, in the operation of a sterilizer, there is a fear that serious troubles such as clogging might occur.

When bubbles are present in the dispersion, the sterilization cannot completely be conducted presumably because the heat is not uniformly distributed in the sterilizer and cannot act on germ cells or spores surrounded by the bubbles.

The protein material dispersed in hot water is, after the dispersion treatment, successively subjected to the sterilization step. A method and a device for the sterilization step are not particularly limited. A continuous sterilization method or a batchwise sterilization method in a device for hydrolysis is useful for smoothly practicing the whole step. The dispersion of the protein material becomes substantially sterile by this sterilization treatment. Further, it is also possible that the sample is collected and identified to be sterile as required.

As a device used for continuous sterilization, a plate-type heat exchanger or a nozzle-type heater is especially appropriate. When the hot water dispersion of the protein material which is produced by the above-mentioned method and is identified to be free from bubbles is treated with these heat sterilization devices under usual operation conditions, accidents such as clogging and scorching in the devices do not occur. Further, cleaning and maintenance procedures of the devices which are conducted after the completion of the treatment are quite easy.

As the fungal culture used in the hydrolysis reaction, a culture newly prepared by growing a fungal strain with a high protease productivity, from which an activity of a protease produced can be anticipated, is appropriate.

As the fungus having the high protease productivity, various fungi can be used regardless of the taxonomical classification. In consideration of the fact that a product is used for food, it is advisable to select fungi which have been used so far in the field of food or brewing industry, especially a koji mold (*Aspergillus*). In practicing the proteolysis reaction, the koji mold is convenient in the aspect of the control of the hydrolysis reaction or the purification and the post-treatment of the reaction product.

As the koji mold, strains newly separated from commercial koji rice and commercial koji for soy sauce brewing and having fixed strain properties may be used. Needless to say, the deposited strains of these microorganisms may be used.

The fungal culture having the high protease activity which is used in the hydrolysis reaction is added to, and mixed with, the protein material which has been sterilized in the form of liquid koji. The starting material constituting the liquid koji may be the same as, or different from, the protein material to be hydrolyzed. However, when the hydrolysis is conducted in a state free from germ contamination, germs should not be present in the liquid koji prepared. Accordingly, special care must be taken in the sterilization of the protein material for preparing liquid koji.

By the way, when there is a fear that the sterilization treatment might not be conducted effectively in the hydrolysis reaction system or when the sterilization treatment cannot satisfactorily be conducted for some reasons, it is also possible to conduct the hydrolysis reaction in the presence of a bacteriostatic substance that inhibits the growth of germs to co-exist in the same system.

Examples of the bacteriostatic substance which is addied to the hydrolysis reaction system include sodium chloride, ethanol and ethyl acetate. Further, with respect to the mode of the addition, appropriate amounts of these bacteriostatic substances are added to the system, and moreover, regarding ethanol, yeast having an ability to form ethanol effectively may be caused to co-exist in the system.

In case any of these bacteriostatic substances is used, there is a need to remove the bacteriostatic substances from the reaction mixture by separation after the completion of the hydrolysis reaction. It is considerably difficult to effectively conduct the removal by separation without decreasing the qualities of the resulting hydrolyzate, and this is not said to be economically advantageous. Especially for completely removing sodium chloride by separation, a new equipment is required. Accordingly, there is no alternative but to obtain a hydrolyzate containing a considerable amount of sodium chloride. The use of such a product is limited as a matter of course.

FIG. 2 is a line graph showing a concentration (unit: mg/dl) of glutamic acid (GH) formed and accumulated in a hydrolysis system at each temperature after each reaction time. Further, FIG. 3 is a line graph showing a concentration (unit: mg/dl) of glucose (Glc) in a hydrolysis system at each temperature after each reaction time.

As is clearly seen upon comparing FIG. 2 with FIG. 3, it can be understood that, by shifting the reaction temperature on purpose during the hydrolysis reaction, the amount of saccharides typified by the concentration of glucose formed and accumulated, especially, the amount of reducing sugars can selectively be reduced without substantially influencing the rate of the proteolysis reaction, namely, the rate of amino acid formation typified by the concentration of glutamic acid formed and accumulated. Further, it can also be understood that the amount and the concentration of sugar present in the reaction product finally obtained can be adjusted to less than predetermined levels.

FIG. 2 reveals that the concentration of glutamic acid formed and accumulated is increased with the increase in the reaction temperature and with the lapse of the reaction time. Meanwhile, FIG. 3 reveals that the concentration of glucose formed and accumulated is abruptly decreased at the reaction temperature of from 36° C. to 39° C. with the lapse of the reaction time (after from 5 to 10 hours). From this fact, it can be anticipated that under the reaction temperature condition of from 36° C. to 39° C., glucose once formed is rapidly decomposed and consumed by the fungi over the course of the reaction time.

That is, the sterile vegetable protein material and the fungal culture, the liquid koji, are mixed in a hydrolysis reaction vessel. Thereafter, the mixture is reacted first at a temperature ranging from 15° C. to 39° C., preferably from 25° C. to 38° C. with aeration and agitation, and the aeration is then stopped to complete the reaction at a temperature ranging from 40° C. to 60° C., preferably from 41° C. to 50° C. Consequently, the amount of sugar, especially reducing sugars, which is formed, accumulated and present in the hydrolysis reaction system, can selectively be decreased without substantially influencing the proteolysis rate, namely the rate of amino acid formation, and the ratio of reducing sugars present in the reaction product finally obtained can be adjusted to 5% or less based on the total solid content in the reaction product.

Moreover, the time when the reaction which is conducted at a temperature ranging from 15° C. to 39° C. is shifted to the reaction which is conducted at a temperature ranging from 40° C. to 60° C. is set at a time when from 10% to 60% of the total period of time required from the start-up to the completion of the reaction passes after the start-up of the reaction. Consequently, the amount of sugar, especially reducing sugars, which is formed, accumulated and present in the hydrolysis reaction system, can selectively be decreased without substantially influencing the proteolysis rate, namely the rate of amino acid formation and the ratio of reducing sugars present in the reaction product finally obtained can be adjusted to 5% or less based on the total solid content in the reaction product.

The hydrolysis reaction product obtained by adjusting the ratio of reducing sugars present in the resulting reaction product to 5% or less based on the total solid content in the reaction product can maintain its quality stably over a long period of time without getting brown.

FIG. 4 is a line graph showing the results of a cruel heating test which was conducted using the above-mentioned product and a control product obtained by conducting the whole procedure at 45° C. constantly without changing the reaction temperature during the hydrolysis reaction.

In FIG. 4, the ordinate axis indicates a rate of increase in an absorbance of light of a wavelength of 545 nm, and the abscissa axis indicates a time for which the temperature is maintained at 105° C. Further, the blank arrow in FIG. 4 shows that the browning of the product could markedly be inhibited as shown by a downward length of the arrow.

This cruel heating test was conducted by maintaining the liquid product and the control liquid product which were adjusted to a 20% Brix concentration in a sealed state at 105° C. for 6 hours. The test conditions correspond to such conditions that the product is maintained at room temperature for 12 months. It suggests that although the product is stored for 12 months, it can keep stable qualities without being browned.

In the hydrolysis reaction, the setting of the two types of the temperature ranges, the setting of the time when the temperature is shifted and the ratio of reducing sugars present in the final reaction product are inductively specified from the results obtained in a large number of trial experiments conducted using various vegetable protein materials and a plurality of liquid kojis of different seed strains under various conditions.

Further, from the results of these many trial experiments, it is advisable to distinguish the above-mentioned two types of the temperature ranges as clearly as possible. That is, it is advisable that the hydrolysis reaction is first started at a relatively low temperature and after the temperature is shifted, the reaction is conducted at a relatively high temperature. Further, in consideration of the fact that the overall period of time required for the hydrolysis reaction is approximately 24 hours in many cases, it has been found that the time when the temperature is shifted is set at a time when approximately 8 hours passes from the start-up of the reaction, that is, a time when approximately 30% of the overall period of time anticipated passes, whereby good results are provided. Still further, the ratio of reducing sugars present in the final reaction product should be 5% or less, preferably 3% or less, more preferably 1.5% or less based on the total solid content. That is, the ratio of 5% is the upper limit thereof.

Accordingly, with respect to the two temperature ranges used when the hydrolysis reaction is conducted with a specific vegetable protein material and a specific liquid koji, and the specific point of time to be set when the temperature is shifted, it is necessary to determine the optimum ranges and the values within the above-mentioned ranges upon conducting preliminary trial experiments on the specific protein materials.

The hydrolyzate obtained under the above-mentioned hydrolysis reaction conditions is a light yellow, semi-transparent liquid having koji mold cells dispersed therein. A light yellow, clear liquid obtained by the solid-liquid separation after the decoloring and deodorizing treatments with the addition of activated carbon is an amino acid solution having a dense, palatable taste, and it is free from a specific unpleasant taste or offensive smell.

The enzymatically hydrolyzed protein solution obtained through the hydrolysis reaction mentioned above is directly used as a seasoning material. However, in many cases, it is subjected to decoloring treatment, deodorizing treatment, for example, activated carbon treatment, or purification treatment such as concentration treatment to provide a product. Alternatively, according to the use Purpose, it is formed into a concentrated paste, a flaky powder, a spray-dried powder, granules or a cubic block. Incidentally, the product obtained without using the bacteriostatic substance such as sodium chloride in the hydrolysis reaction step has multi-purpose characteristics for which it can find wide acceptance, in addition to the property that it is not browned easily.

BEST MODE FOR CARRYING OUT THE INVENTION

Figure 1:
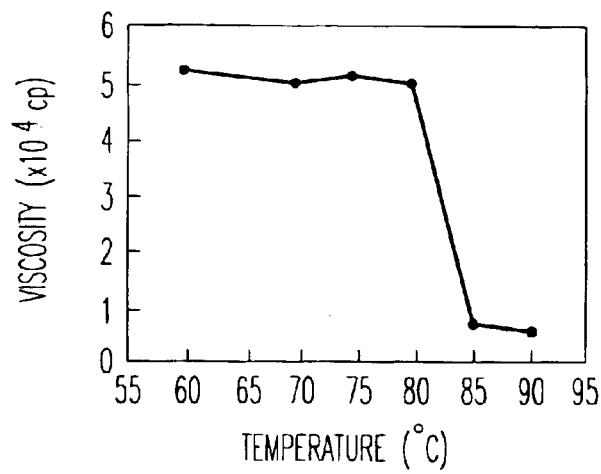
FIG. 1 is a line graph showing the relationship of viscosity and temperature of a dispersion of wheat protein in hot water.
Figure 2:
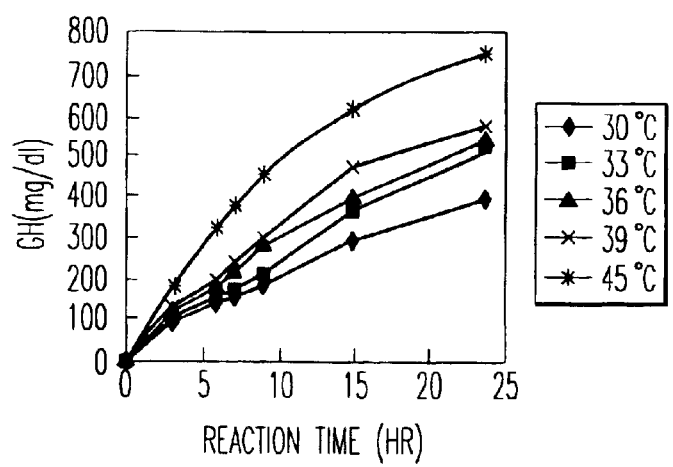
FIG. 2 is a line graph showing a relationship of a concentration of glutamic acid formed and accumulated in a hydrolysis reaction system when employing various reaction temperatures and a reaction time.
Figure 3:
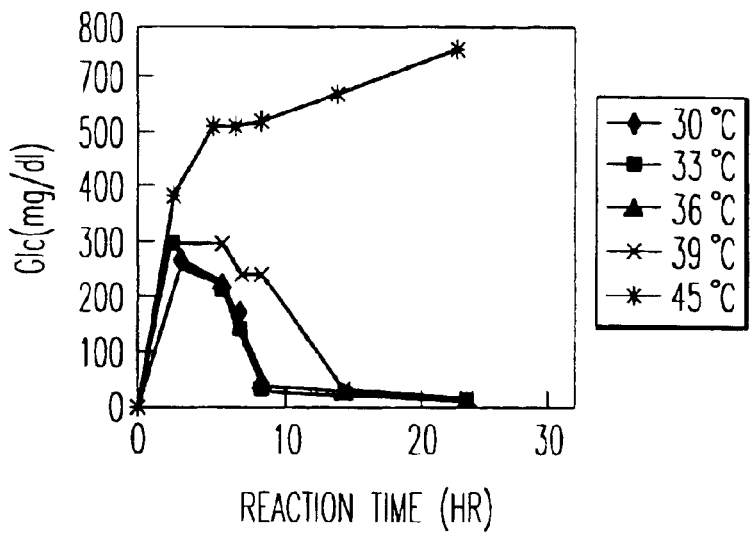
FIG. 3 is a line graph showing a relationship of a concentration of glucose formed and accumulated in a hydrolysis reaction system when employing various reaction temperatures and a reaction time.
Figure 4:
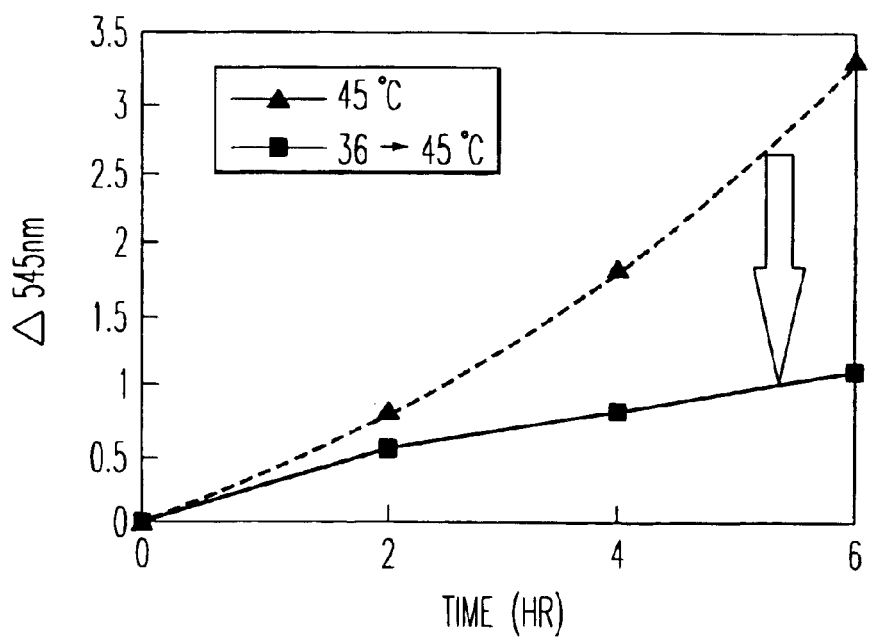
FIG. 4 is a line graph showing that there is a marked difference in the increase of an absorbance in a cruel heating test conducted with respect to a product obtained by shifting hydrolysis reaction temperature conditions during the reaction and a product obtained by not shifting the temperature conditions.

The invention is illustrated by referring to specific Examples of the invention. By the way, the following Examples do not limit the technical scope of the invention.

EXAMPLE 1

Production of a Wheat Gluten Hydrolyzate Resistant to Browning (Emulsification Pretreatment of Wheat Gluten)

Four-hundred liters of city water were introduced into a 1,000-liter tank connected with an emulsifier for emulsification by impact shearing, Homomicline Mill (supplied by Tokushu Kikako K.K.). Water in the tank was heated. When the temperature of water reached 95° C., the operation of the emulsifier started. Twenty kilograms of a powder of active wheat gluten were charged into the tank. The wheat gluten became a completely emulsified dispersion in 30 minutes after the operation started, and at the same time, the viscoelasticity peculiar to wheat gluten disappeared. In the dispersion, neither incorporation of a coagulum (so-called clump) of wheat gluten nor inclusion of bubbles was observed at all in a slightly enlarged visual field of a microscope.

The particle diameter of the wheat gluten particles in the emulsified dispersion was on the average 150 μm, at least 10 μm and at most 900 μm. Further, the concentration of the wheat gluten particles was 50 g/liter.

(Pretreatment of De-fatted Soybeans for Liquid Koji) A de-fatted soybean powder obtained by roughly pulverizing unmodified de-fatted soybeans (supplied by Toyo Seiyu K.K.) was heated while being mixed with a mixer capable of heating procedure to conduct hot heat treatment at 98° C. for 20 minutes. (Sterilization Treatment of De-fatted Soybeans for Liquid Koji)

Three kilograms of the de-fatted soybean powder heat-treated were charged into 200 liters of water having a temperature of 25° C. which had been introduced into a submerged culture fermenter-type reaction vessel for amino acid production while being stirred to obtain a uniform de-fatted soybean powder dispersion free from inclusion of bubbles. Subsequently, the dispersion was subjected to batchwise heat sterilization through heating with a superheated steam at 120° C. for 20 minutes.
(Production of Liquid Koji)

One percent by volume of a seed culture of a koji mold, *Aspergillus oryzae* ATCC 15240, which had been incubated after inoculating spores at a concentration of $10^4$ spores/ml in a medium containing 1.5% de-fatted soybean powder in a 5-liter jar fermenter, was inoculated in this heat-sterilized dispersion of de-fatted soybean powder. After the inoculation, the cultivation was conducted at 30° C. for 24 hours with aeration at a rate of ¼ vvm and agitation at 520 rpm to obtain liquid koji.
(Evaluation of Liquid Koji)

The protease activity of the resulting liquid koji was 304 units/ml, and neither contamination of germs other than the koji mold nor growth thereof was observed.
(Hydrolysis of Wheat Gluten)

The total amount of the wheat gluten emulsified dispersion obtained by the above-mentioned method was transferred to a 1-kiloliter fermenter used in fermentation for amino acid production. Subsequently, the wheat gluten dispersion was subjected to batchwise heat sterilization through heating with a superheated steam at 120° C. for 20 minutes. When the temperature of the solution was lowered to 50° C. after the completion of the heat sterilization, the half amount of the liquid koji was added thereto. The hydrolysis reaction was conducted until hour 8 from the start-up of the reaction with aeration at a rate of ¼ vvm and agitation at 200 rpm while controlling the temperature of the dispersion to 35° C., and from hour 8 to hour 24 when the reaction was completed, without conducting the aeration while controlling the temperature of the dispersion to 45° C.

During the reaction, the concentration of amino acids formed in terms of the glutamic acid concentration in the reaction system was progressively increased from the start-up of the reaction. Meanwhile, the concentration of reducing sugars in terms of the glucose concentration in the reaction system was rapidly increased until hour 3 from the start-up of the reaction and was maintained approximately at the maximum value from then to hour 8. However, while the reaction was continued upon raising the temperature of the dispersion in the reaction system from hour 8 and maintaining and controlling it to 45° C., the concentration of reducing sugars was abruptly decreased. On hour 24 when the reaction was completed, the glucose concentration was decreased to 1.0% by weight or less based on the total solid content of the reaction product.
(Hydrolysis of Wheat Gluten Conducted as a Control)

Two-hundred liters of a wheat gluten emulsified dispersion which had been obtained in the above-mentioned manner were charged into a 1-kiloliter fermenter used in fermentation of an amino acid. Then, the wheat gluten dispersion was subjected to batchwise heat sterilization through heating with a superheated steam at 120° C. for 20 minutes. When the temperature of the dispersion was lowered to 50° C. after the heat sterilization, the half amount of the liquid koji was added thereto. The hydrolysis reaction was conducted with aeration and agitation while maintaining the temperature of the dispersion at 45° C. constantly and without shifting the temperature during the whole reaction period from the start-up of the reaction to hour 24 when the reaction was completed.

During the reaction, the concentration of amino acids in terms of the glutamic acid concentration in the reaction system was progressively increased from the start-up of the reaction. Meanwhile, the concentration of reducing sugars in terms of the glucose concentration in the reaction system was rapidly increased until hour 3 from the start-up of the reaction and was maintained at approximately the maximum value from hour 8 to hour 24 when the reaction was completed. On hour 24 when the reaction was completed, the glucose concentration reached 6.6%. It was identified that during the overall reaction period, the glutamic acid concentration tended to be always increased somewhat slowly in comparison with the above-mentioned case of raising and controlling the temperature of the solution during the reaction. (Test for Storage of the Hydrolyzate Obtained)

The test hydrolyzate of wheat gluten (hereinafter referred to as a "test product") obtained by the above-mentioned method and the control hydrolyzate of wheat gluten (hereinafter referred to as a "control product") for comparison were subjected to centrifugation to separate and remove the koji mold cells. The residues were then passed through a granular activated carbon layer for brewing to obtain hydrolyzates purified. Each of these hydrolyzates purified was charged into a 500-milliliter colorless transparent glass bottle having a stopper such that no space was given on the upper portion.

With respect to the samples in the bottles stored under scattered light in a room in which the temperature was not particularly controlled, the state of occurrence and progression of browning was visually observed immediately after the charging and after 1 week, 2 weeks, 1 month, 3 months, 6 months and 12 months. The results are shown in Table 1 together with the state of the change of a smell immediately after releasing the stopper after these storage periods. In Table 1, "+" in the column "browning" indicates evaluation with 5 grades. That is, a state in which browning proceeds most is defined as 5, and a state in which browning is slightly observed is defined as 1. Further, "+" in the column "burnt smell" indicates evaluation with 5 grades. That is a state in which an irritating smell accompanied by browning, a so-called "burnt smell" notably occurs is defined as 5, and a state in which the burnt smell is slightly found is defined as 1. By the way, the evaluation was conducted by five panelists. The evaluation points given by the panelists were averaged, and rounded. The resulting points were indicated in terms of the number of "+".

TABLE 1

Browning of a wheat gluten hydrolyzate

| | Test product | | Control product | |
|---|---|---|---|---|
| Storage period | Browning | Burnt smell | Browning | Burnt smell |
| Immediately after charging | No | No | No | No |
| After 1 week | No | No | No | + |
| After 2 weeks | No | No | + | + |
| After 1 month | No | No | ++ | + |
| After 3 months | No | No | +++ | ++ |
| After 6 months | + | No | ++++ | +++ |
| After 12 months | + | + | +++++ | +++++ |

As shown in Table 1, in the test product, even after 12 months, the degree of browning was week, and the occurrence of the "burnt smell" was little found. Thus, the test product was judged to maintain a satisfactory commercial value. Meanwhile, in the control product, immediately after the charging into the bottle, the sign of the browning was already observed, and the presence of the "burnt smell" was found though weak. After 1 month, the "browning" and the "burnt smell" were clearly found. After 3 months, the "browning" and the "burnt smell" were both notably found. Accordingly, the control product was judged to extremely impair a commercial value.

EXAMPLE 2

Production of Hydrolyzed Protein Resistant to Browning from the Other Vegetable Protein Materials Hydrolyzed protein resistant to browning were produced from corn gluten and de-fatted soybeans in the same manner as in Example 1.

(Pretreatment of Vegetable Protein Materials)

Powdery corn gluten from Minnesota, U.S.A. was emulsified as in Example 1. Further, unmodified de-fatted soybeans (supplied by Toyo Seiyu K.K.) were pulverized, and then emulsified as in Example 1. Neither formation of a coagulum (so-called a clump) nor inclusion and presence of bubbles was observed at all in any of the emulsified products.

(Production of Liquid Koji)

Liquid koji was produced from the de-fatted soybean powder in the same manner as in Example 1.

(Hydrolysis of the Vegetable Protein Materials)

Each of the corn gluten emulsified dispersion and the de-fatted soybean emulsified dispersion was transferred to a 30-kiloliter fermenter, and sterilized. When the temperature of the dispersion was lowered to 50° C., the liquid koji was added to each of the fermenters as in Example 1. The conditions of the hydrolysis reaction were the same as those in Example 1. That is, the hydrolysis reaction was conducted until hour 8 from the start-up of the reaction with aeration and agitation while controlling the temperature of the dispersion to 35° C., and from hour 8 to hour 24 when the reaction was completed without aeration while controlling the temperature of the dispersion to 45° C. In the completion of the hydrolysis reaction, the glucose concentration of the reaction product was 0.9% by weight based on the total solid content of the reaction product.

(Hydrolysis of the Vegetable Starting Materials Conducted as a Control)

Each of a corn gluten emulsified dispersion and a defatted soybean emulsified dispersion obtained according to the above-mentioned method was transferred to a 30-kiloliter fermenter, and sterilized. When the temperature of the dispersion was lowered to 50° C., the liquid koji was added to each fermenter. The hydrolysis reaction was conducted with agitation while controlling the temperature of the dispersion to 45° C. without shifting the temperature during the reaction from the start-up of the reaction to hour 24 when the reaction was completed. When the hydrolysis reaction was completed, the glucose concentration in the reaction product was 6.4% by weight based on the total solid content.

(Test for Storage of the Resulting Hydrolyzates)

The resulting hydrolyzates were subjected to the storage test in the same manner as in Example 1. The results thereof for comparison are shown in Tables 2 and 3.

TABLE 2

Browning of a corn gluten hydrolyzate

| Storage period | Test product | | Control product | |
|---|---|---|---|---|
| | Browning | Burnt smell | Browning | Burnt smell |
| Immediately after charging | No | No | No | No |
| After 1 week | No | No | No | No |
| After 2 weeks | No | No | + | + |
| After 1 month | No | No | ++ | + |
| After 3 months | No | No | +++ | ++ |
| After 6 months | + | No | ++++ | +++ |
| After 12 months | + | + | +++++ | +++++ |

TABLE 3

Browning of a de-fatted soybea hydrolyzate

| Storage period | Test product | | Control product | |
|---|---|---|---|---|
| | Browning | Burnt smell | Browning | Burnt smell |
| Immediately after charging | No | No | No | No |
| After 1 week | No | No | > | > |
| After 2 weeks | No | No | + | + |
| After 1 month | No | No | ++ | ++ |
| After 3 months | No | No | +++ | +++ |
| After 6 months | + | No | ++++ | ++++ |
| After 12 months | + | + | +++++ | +++++ |

As shown in Tables 2 and 3, in the corn gluten test product and the de-fatted soybean test product, even after 12 months, the degree of browning was week and the occurrence of the "burnt smell" was little found. Thus, the test products were judged to maintain a satisfactory commercial value. Meanwhile, in the gluten control product and the de-fatted soybean control product, immediately after the charging into the bottle, the sign of the browning was already observed though there was a slight difference therebetween, and the presence of the "burnt smell" was found though weak. After 1 month, the "browning" and the "burnt smell" were clearly found. After 3 months, the "browning" and the "burnt smell" were both notably found. Accordingly, the control products were judged to extremely impair a commercial value.

INDUSTRIAL APPLICABILITY

Hydrolyzed protein produced from a vegetable protein material in a liquid reaction system using a fungal culture according to the method of the present invention can maintain a stable commercial value without being browned over a long period of time.

What is claimed is:

1. A method for producing hydrolyzed protein by subjecting a vegetable protein material containing saccharides to enzymatic hydrolysis, comprising:
    (1) conducting cultivation of a koji mold in a submerged culture fermenter-type reaction vessel to obtain a fungal culture;
    (2) mixing a dispersion of said vegetable protein material with said fungal culture to obtain a mixture; and
    (3) subjecting said mixture to enzymatic hydrolysis first at a temperature ranging from 15° C. to 39° C. with aeration and agitation and then at a temperature ranging from 41° C. to 50° C.,
    to obtain said hydrolyzed protein,
    wherein a ratio of reducing sugars present in said hydrolyzed protein obtained is 5% by weight or less based on the total solid content in said hydrolyzed protein, and
    wherein the temperature is shifted from a temperature ranging from 15° C. to 39° C. to a temperature ranging from 41° C. to 50° C. when from 10% to 60% of the total period of time required for completion of the enzymatic hydrolysis has passed;
    wherein each of (1) to (3) are in a liquid state,
    wherein said vegetable protein material is prepared for said enzymatic hydrolysis by a process comprising:
    (a) pulverizing a vegetable protein material which exists at least partially in a solid state to a size of 300 μm or less to obtain pulverized vegetable protein material;
    (b) dispersing said pulverized vegetable protein material in hot water at a temperature higher than 80° C., to obtain a vegetable protein material dispersion;
    (c) removing air bubbles from said vegetable protein material dispersion; and
    (d) subjecting said vegetable protein material dispersion to sterilization immediately after said air bubbles have been substantially removed
    and wherein said method is in the absence of an added bacteriostatic substance.

2. The method of claim 1, wherein said vegetable protein material is selected from the group consisting of wheat gluten, corn gluten, de-fatted soybean, and treated products thereof.

3. The method of claim 1, wherein said subjecting said mixture to enzymatic hydrolysis is first at a temperature ranging from 25° C. to 38° C. with aeration and agitation.

4. The method of claim 1, wherein said enzymatic hydrolysis is completed at a temperature ranging from 41° C. to 50° C.

5. The method of claim 1, wherein said subjecting said mixture to enzymatic hydrolysis is first at a temperature ranging from 25° C. to 38° C. with aeration and agitation, and wherein said enzymatic hydrolysis is completed at a temperature ranging from 41° C. to 50° C.

6. The method of claim 1, wherein said enzymatic hydrolysis is first at a temperature ranging from 15° C. to 39° C. and is shifted to a temperature ranging from 41° C. to 50° C. so that the ratio of reducing sugars present in said hydrolyzed protein obtained at the completion of said enzymatic hydrolysis is 3% by weight or less based on the total solid content in said hydrolyzed protein.

7. The method of claim 1, wherein said enzymatic hydrolysis is first at a temperature ranging from 15° C. to 39° C. and is shifted to a temperature ranging from 41° C. to 50° C. so that the ratio of reducing sugars present in said hydrolyzed protein obtained at the completion of said enzymatic hydrolysis is 1.5% by weight or less based on the total solid content in said hydrolyzed protein.

* * * * *